US008722242B2

(12) United States Patent
Muldoon et al.

(10) Patent No.: US 8,722,242 B2
(45) Date of Patent: May 13, 2014

(54) ELECTROLYTE FOR MAGNESIUM BATTERY

(75) Inventors: John Muldoon, Saline, MI (US); Claudiu Bogdan Bucur, Ypsilanti, MI (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 363 days.

(21) Appl. No.: 13/198,580

(22) Filed: Aug. 4, 2011

(65) Prior Publication Data

US 2013/0034780 A1    Feb. 7, 2013

(51) Int. Cl.
*H01M 6/04* (2006.01)

(52) U.S. Cl.
USPC ........... 429/188; 429/324; 429/206; 429/239; 429/231.6; 429/218.1

(58) Field of Classification Search
CPC .............................. H01M 4/466; H01M 4/136
USPC ........... 429/339, 188, 218.1, 231.6, 239, 324, 429/206
See application file for complete search history.

(56) References Cited

U.S. PATENT DOCUMENTS

| | | | |
|---|---|---|---|
| 2008/0182176 A1 | 7/2008 | Aurbach et al. | |
| 2011/0159381 A1 | 6/2011 | Doe et al. | |
| 2011/0244338 A1 | 10/2011 | Muldoon et al. | |
| 2011/0262804 A1* | 10/2011 | Muldoon et al. | 429/207 |

FOREIGN PATENT DOCUMENTS

| | | |
|---|---|---|
| JP | 2004-265675 | 9/2004 |
| WO | WO 2011/137158 | * 11/2011 |

OTHER PUBLICATIONS

Z. Lu, et al. "On the Electrochemical Behavior of Magnesium Electrodes in Polar Aprotic Electrolyte Solutions" Journal of Electroanalytical Chemistry, vol. 466, (pp. 203-217) 1999.
D. Aurbach, et al. "Prototype Systems for Rechargeable Magnesium Batteries" Nature, vol. 407, (pp. 724-727) 2000, www.nature.com.
Thomas D. Gregory, et al. "Nonaqueous Electrochemistry of Magnesium" J. Electrochem. Soc., vol. 137, No. 3, (pp. 775-780), 1990.
D. Aurbach, et al. "The Study of Reversible Magnesium Deposition by In Situ Scanning Tunneling Microscopy", Electrochemical and Solid-State Letters, 4 (8) A113-A116 (2001).
Kang Xu; "Nonaqueous Liquid Electrolytes for Lithium-Based Rechargeable Batteries", Chem. Rev., 104, pp. 4303-4417, 2004.
Hee Soo Kim, et al., "Structure and compatibility of a magnesium electrolyte with a sulphur cathode", Nature Communications, pp. 1-6, 2011, www.nature.com/naturecommunications.
U.S. Appl. No. 12/768,017, filed Apr. 27, 2010, Muldoon, et al.

* cited by examiner

*Primary Examiner* — Patrick Ryan
*Assistant Examiner* — Alex Usyatinsky
(74) *Attorney, Agent, or Firm* — Oblon, Spivak, McClelland, Maier & Neustadt, L.L.P.

(57) ABSTRACT

A magnesium battery, having an anode containing magnesium; a cathode stable to a voltage of at least 2.6 V relative to a magnesium reference; and an electrolyte containing an electrochemically active magnesium salt obtained by reaction of a Grignard reagent or Hauser base with a boron compound of formula $BR_3$ is provided. The electrolyte is stable to 2.6 E.V. vs. Mg in the presence of stainless steel.

18 Claims, 2 Drawing Sheets

ELECTROLYTE FOR MAGNESIUM BATTERY

BACKGROUND OF THE INVENTION

1. Field of the Invention

Increasing costs of traditional fuels along with high atmospheric pollution amplify the need for efficient methods of energy capture for cheap, renewable, environmentally friendly power sources. High energy density batteries are conventionally employed for energy storage and release and may be viable energy sources in the future.

Lithium ion batteries have been in commercial use since 1991 and have been conventionally used as power sources for portable electronic devices. The technology associated with the construction and composition of the lithium ion battery (LIB) has been the subject of investigation and improvement and has matured to an extent where a state of art LIB battery is reported to have up to 700 Wh/L of energy density. However, even the most advanced LIB technology is not considered to be viable as a power source capable to meet the demands for a commercial electric vehicle (EV) in the future. As this energy density is close to the theoretical limit of a lithium ion active material, technologies which can offer battery systems of higher energy density are under investigation.

2. Discussion of the Background

Alkaline earth metals provide attractive anode choices as alternative materials to lithium, for the development of high capacity batteries. Mg is the most attractive and interesting of the alkaline earth metals in this regard because Mg potentially has a volumetric capacity of 3832 mAh cm$^{-3}$ which is significantly greater than the 2062 mAh cm$^{-3}$ of Li. Additionally, Mg has a negative reduction potential of −2.356V vs NHE. As the seventh most abundant element in the earth's crust, Mg has a lower resource cost and a lower environmental impact profile (see Aurbach: Nature, Vol 407, pp 724-727, 2000).

Significantly, Mg does not suffer from dendrite formation, which renders Li metal unsafe for commercialization as a high capacity anode material (West: Journal of Electrochemical Communications, Vol 155, pp A806-A811, 2008). Consequently, to avoid this problem, conventional Li ion batteries utilize graphite anodes having a volumetric capacity of only 777 mAh cm$^{-3}$ (Aurbach: Electrochemical Solid-State Letters, Volume 4, pp A113-A116, 2001).

The electrochemical behavior of a magnesium electrode in a polar aprotic electrolyte solution was reported by Lu et al. in the Journal of Electroanalytical Chemistry (466 (1999) pp 203-217). These authors concluded that the electrochemical behavior of Mg is different from that of Li in polar aprotic electrolyte solutions. Their investigation showed that in contrast to the case of lithium electrodes, surface films which form on the Mg electrode in the aprotic solvents do not transport Mg ions. Therefore, conventional electrolyte systems employed in lithium transport systems are not suitable for a cell having a magnesium anode. Since Mg ion transport is an essential requirement for any electrochemical cell based on a magnesium anode, other electrolyte systems have been investigated.

Gregory et al. (J. Electrochem. Soc., 137 (3), March, 1990, 775-780) reported electrolyte systems of alkylmagnesium halide-organoboron complexes in an ether solvent. Also reported were alkylmagnesium halide solutions to which aluminum halides were added. Mg dissolution and plating at very high current efficiencies, giving bright crystalline Mg deposits were obtained in these systems. However, a suitable cathode material, compatible with the electrolyte system was not reported.

The most commonly used magnesium electrolyte to date is an in-situ generated organometallic material such as phenyl magnesium chloride/aluminum chloride in tetrahydrofuran. However, these electrolyte mixtures are not likely to be of practical commercial utility due to air and moisture sensitivity characteristic of such Grignard-based materials. Moreover, the in-situ generated electrolytes based on reaction of phenyl magnesium chloride/aluminum chloride electrolyte have limited anodic stability, and significantly, such materials are highly nucleophilic and intrinsically strong reducing agents. This chemical reactivity character may be problematic, because to construct an electrochemical cell employing a Grignard type electrolyte, a cathode material which is essentially chemically inert to the Grignard based electrolyte may be required.

Aurbach et al. (NATURE, 407, Oct. 12, 2000,724-726) describes an Mg battery system containing a magnesium organohaloaluminate salt in tetrahydrofuran (THF) or a polyether of the glyme type as electrolyte and a $Mg_xMo_3S_4$ cathode based on a $Mo_3S_4$ Chevrel phase host material. A similar cathode material described as having a formula $Mg_{(0-2)}MO_6S_{(8-n)}Se_n$ was also reported by Aurbach (Advanced Materials, 19, 2007, 4260-4267).

U.S. Pre-Grant Publication No. 2008/0182176 to Aurbach et al. describes an electrochemical cell having a magnesium anode and an intercalation cathode having a modified Chevrel phase. The Chevrel phase compound is represented by the formula $Mo_6S_{8-y}Se_y$ (y is greater than 0 and less than 2) or $M_xMo_6S_8$ (x is greater than 0 and less than 2). The electrolyte is represented by the formula Mg $(AlR_xCl_{4-x})2$ and/or $(MgR_2)_x$-$(AlCl_{3-n}R_n)_y$, wherein R is methyl, ethyl, butyl, phenyl and derivatives thereof, n is greater than 0 and lower than 3, x is greater than 0 and lower than 3 and y is greater than 1 and lower than (claim 3) in an ether solvent.

From a practical point of view, with regard to production and use of a commercial battery, electrolyte systems containing agents such as dibutyl magnesium are problematic because of corrosivity, inhalation hazard, flammability and moisture sensitivity.

JP 2004-265675 to Hideyuki et al. describes a test cell constructed with a sulfur containing anode and a negative electrode of magnesium metal. Magnesium bis(trifluoromethylsulfonyl)imide in γ-butyrolactone is employed as an electrolyte system.

However, Mg batteries cannot utilize commercially available aprotic ionic salts such as magnesium bis(trifluoromethanesulfonyl)-imide and magnesium perchlorate because of the reported formation of a solid electrolyte interface (SEI) film impermeable to Mg ions which prohibits deposition/dissolution (Feng, Z: Surface Coating Technologies, Vol 201, pp 3783-3787, 2006).

The ideal Mg battery electrolyte would be electrochemically and chemically stable in battery operation conditions, would have high ionic conductivity but be an electronic insulator, contain ions of the Mg anode material and have low melting and high boiling points (Xu, K: Chemical Reviews, Vol 104, pp 4303-4417, 2004). This electrolyte would also need to be inert to battery components such as anode, cathode or current collector. Aurbach et al. was the first to report a family of magnesium organohaloaluminate electrolytes which are compatible with magnesium anodes (Aurbach: Nature, Vol 407, pp 724-727, 2000, Aurbach: 6,316,141). They are generated in situ from the reaction between a Lewis acid and a Lewis base such as phenylmagnesiumchloride and aluminum trichloride (AlCl$_3$), respectively, in tetrahydrofuran. Muldoon et al. was the first to report the crystallization of the electrochemically active species (Mg$_2$(μ-Cl)$_3$.6THF)(HMDS$_n$AlCl$_{4-n}$) (n=1, 2), formed from the reaction of hexamethyldisilizide (HMDSMgCl) and AlCl$_3$ in tetrahydrofuran. (Muldoon: *Nature Communications* 10.1038/ncomms1435, 2011; U.S. application Ser. No. 12/758,343, filed Apr. 12, 2010; U.S. application Ser. No. 12/768,017, filed Apr. 27, 2010). However, while these electrolytes have voltage stabilities above 3V vs Mg on a Pt working electrode, their voltage stability drops to 2.3V vs Mg on stainless steel working electrode (FIG. 1).

The stainless steel compatibility problem may be overcome by using carbon cloth current collectors (Muldoon: Nature Communications, 10.1038/ncomms1435). Doe et al. (U.S. 2011/0159381, filed Mar. 8, 2011) reports the dependence of the oxidative stability of Mg organohaloaluminates electrolytes on a variety of metals and describes a magnesium battery electrode assembly having a current collector containing a carbonaceous material to avoid this problem.

However, improving the voltage stability of magnesium electrolytes on stainless steel is crucial because stainless steel is a widely used current collector and a major component in a variety of batteries such as coin cells. Current state of the art magnesium organohaloaluminate electrolytes limit the usage of Mg battery coin cells to operating under 2.3V vs Mg.

SUMMARY OF THE INVENTION

Therefore, an object of the present invention is to provide an electrolyte system which efficiently transports Mg ions, is compatible with magnesium and other battery components, including stainless steel, is safe to handle and imparts low environmental impact.

This and other objects have been achieved by the present invention, the first embodiment of which includes a magnesium battery, comprising:
a negative electrode comprising magnesium;
a positive electrode which is stable to 2.6 E.V. vs. Mg;
a solvent; and
an electrolyte of formula (I):

[Mg$_2$(μ-Cl)$_3$.6THF][BR$_4$]     (I)

wherein

R is each independently a C(1-12) alkyl or C(6-10) aryl group, optionally substituted with alkoxy, cyano, nitro or C(1-6) alkyl groups.

In a further embodiment of the invention, the magnesium battery contains at least one stainless steel component and in a preferred embodiment the current collector for the magnesium battery is stainless steel.

In another preferred embodiment, the invention includes a magnesium battery, wherein
the negative electrode is magnesium,
the positive electrode comprises a stainless steel current collector coated with a composition comprising sulfur, and
the electrolyte of formula (I) is

[Mg$_2$(μ-Cl)$_3$.6THF][B(C$_6$H$_5$)$_4$]     (II).

DETAILED DESCRIPTION OF THE INVENTION

The invention provides a novel Mg electrolyte of formula (I);

[Mg$_2$(μ-Cl)$_3$.6THF][BR$_4$]     (I)

wherein

R is each independently a C(1-12) alkyl or C(6-10) aryl group, optionally substituted with alkoxy, cyano, nitro or C(1-6) alkyl groups and a magnesium battery containing the magnesium battery of formula (I).

In a first embodiment the invention provides a magnesium battery, comprising:
a negative electrode comprising magnesium;
a positive electrode which is stable to 2.6 E.V. vs. Mg;
a solvent; and
an electrolyte of formula (I):

[Mg$_2$(μ-Cl)$_3$.6THF][BR$_4$]     (I)

wherein

R is each independently a C(1-12) alkyl or C(6-10) aryl group, optionally substituted with alkoxy, cyano, nitro or C(1-6) alkyl groups.

In preferred embodiments of the invention R in formula (I) may be methyl ethyl and propyl. In other preferred embodiments, R may be a phenyl group, a methyl substituted phenyl or a dimethyl substituted phenyl.

In a further embodiment of the invention, the magnesium battery contains at least one stainless steel component and in a preferred embodiment the current collector for the magnesium battery is stainless steel.

As an example according to the present invention, a novel magnesium electrolyte may be formed by reaction of triphenylboron with phenylmagnesiumchloride. Crystallization of the product of this reaction yields a product of the following formula:

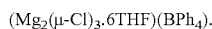

(Mg$_2$(μ-Cl)$_3$.6THF)(BPh$_4$).

The separated electrochemically active salt may be washed with conventionally known solvents and/or recrystallized from conventionally known solvents.

Figure 1:
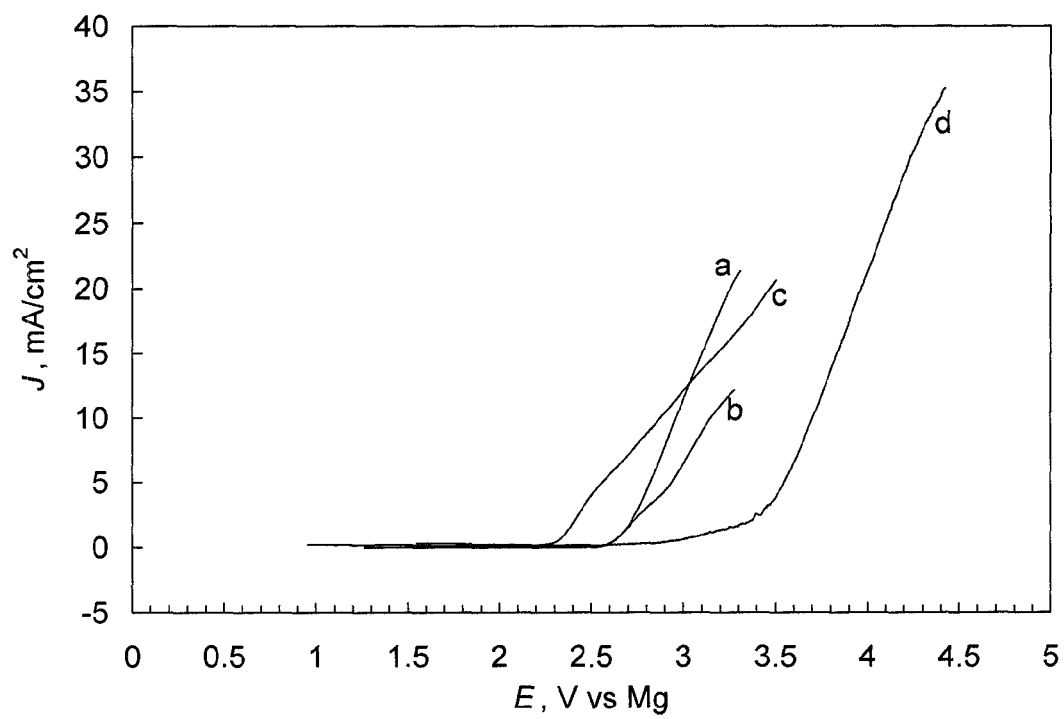
FIG. 1 shows the comparative oxidative stability of (Mg$_2$(μ-Cl)$_3$.6THF)(BPh$_4$) and (Mg$_2$(μ-Cl)$_3$.6THF)(HMDS$_n$AlCl$_{4-n}$) on stainless steel and Pt.
Figure 3:
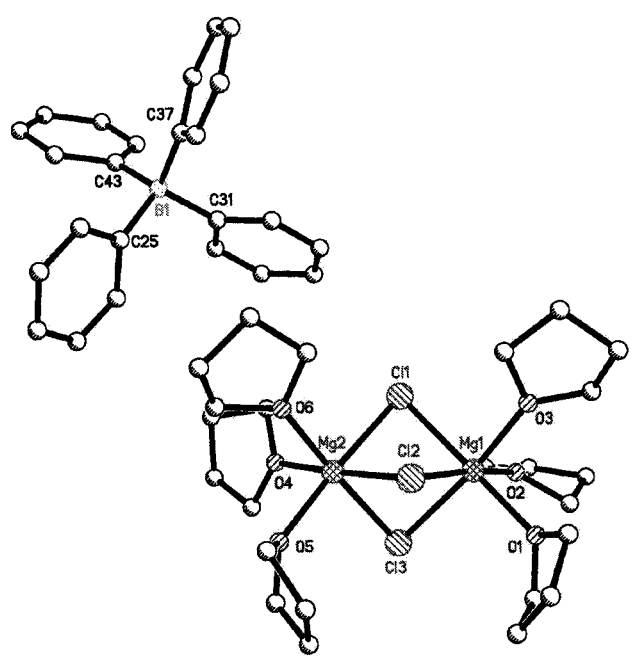
FIG. 3 shows the crystal structure of (Mg$_2$(μ-Cl)$_3$.6THF)(BPh$_4$)

The structure of this compound was confirmed by single X ray diffraction where the anion showed a boron atom tetrahedrally coordinated to four phenyl groups (FIG. 3). The cation consisted of two tetrahedrally coordinated Mg centers bridged by three chloride atoms. The remaining three sites on each Mg are coordinated by tetrahydrofuran through the oxygen moiety. Mass spectrometry analysis showed an exact mass and isotope pattern consistent with the BPh$_4^-$ anion. The electrochemistry of this electrolyte is superior and extremely unique when compared to Mg organohaloaluminates electrolytes previously reported by Aurbach and Muldoon. As indicated in FIG. 1 the electrolyte has a higher oxidative stability on stainless steel (2.6V vs Mg) which is also identical to its oxidative stability on Pt, suggesting true inertness towards stainless steel. This electrolyte is soluble in ether containing solvents such as tetrahydrofuran, polyethers, 2-methyl tetrahydrofuran, dimethoxyethane, dimethyl glycol, glyme, monoglyme, ethylene glycol, dimethyl ether, diethyl ether, ethyl glyme, diglyme, proglyme, ethyl diglyme, triglyme, butyl diglyme, tetraglyme, polyglyme, highlyme or combinations thereof. One can also dissolve this salt (Mg$_2$(μ-Cl)$_3$.6THF)(BPh$_4$) in an ether containing solvent and soak it in a polymer film to form a polymer based electrolyte.

FIG. 1 shows the Oxidative stability of the prepared (Mg$_2$(μ-Cl)$_3$.6THF)(BPh$_4$) on stainless steel (a) and Pt (b) and of (Mg$_2$(μ-Cl)$_3$.6THF)(HMDS$_n$AlCl$_{4-n}$) (n=1, 2) on stainless steel (c) and Pt (d). Linear scan voltammograms were conducted on a Pt electrode with 0.02 cm$^2$ surface area, at 25 mV s$^{-1}$, ° C. with a Mg reference and counter electrode.

Figure 2:
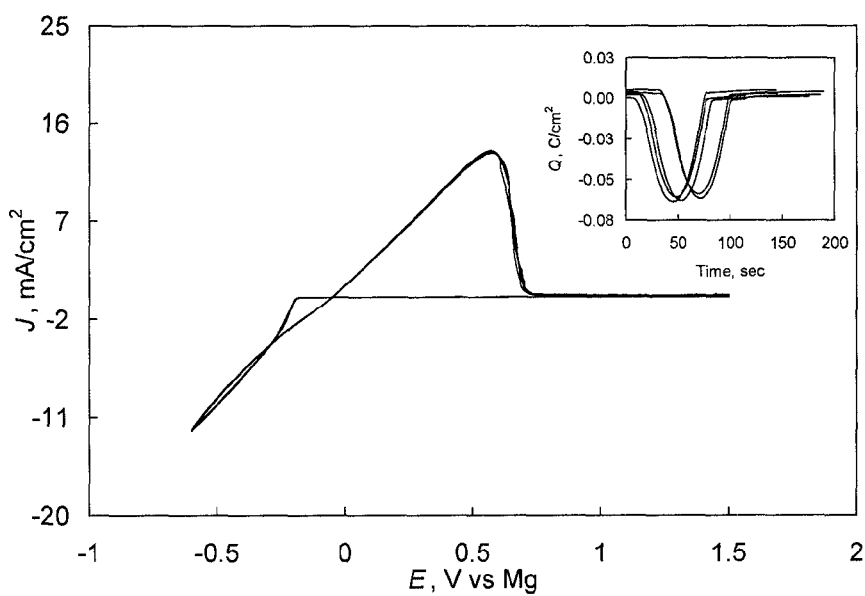
FIG. 2 shows a cyclicvoltammogram stability study of (Mg$_2$(μ-Cl)$_3$.6THF)(BPh$_4$)

FIG. 2 shows five deposition/dissolution cycles of Mg in (Mg$_2$(μ-Cl)$_3$.6THF)(BPh$_4$) electrolyte and demonstrates a 100% coulombic efficiency (inset) is obtained. The cyclic voltammograms were conducted on a Pt electrode with 0.02 cm$^2$ surface area, at 25 mV s$^{-1}$, ° C. with a Mg reference and counter electrode.

FIG. 3 shows the single X ray diffraction of crystallized (Mg$_2$(μ-Cl)$_3$.6THF)(BPh$_4$) as an ORTEP plot, with 25% thermal probability ellipsoids. In the Figure, hydrogen atoms are omitted for clarity.

This chemistry may be easily expanded to include Lewis acids of boron (BR$_3$) or aluminum (AlR$_3$) where various R groups such as methyl, ethyl, butyl or aryl, benzyl, amido, naphthal, phenyl, alkenyl and other derivatives thereof can be attached, including fluorinated derivatives. Also, various Grignard or Hauser Lewis bases of formula R$_2$NMgCl where R is alkyl or aromatic may be utilized. Unlike previous magnesium electrolytes with reduced voltage stability on stainless steel, this electrolyte, (Mg$_2$(μ-Cl)$_3$.6THF)(BPh$_4$) has identical voltage stability on a wide variety of working electrodes, including stainless steel (FIG. 1). As indicated in FIG. 1, the (Mg$_2$(μ-Cl)$_3$.6THF)(BPh$_4$) electrolyte is compatible with a magnesium anode and with stainless steel. Its voltage stability on stainless steel (and Pt) is 2.6V vs. Mg (FIG. 1) and the coulombic efficiency is about 100% (FIG. 2).

Such performance allows the construction of a magnesium battery with any metal component parts which are stable to 2.6 V vs. Mg, including stainless steel.

According to the above first embodiment, the positive electrode of the Mg battery may contain any positive electrode active material which is stable to 2.6 V vs. Mg. Examples of such positive electrode active material may include sulfur, Chevrel phase Mo$_6$S$_8$, MnO$_2$, CuS, Cu$_2$S, Ag$_2$S, CrS$_2$, VOPO$_4$, layered structure compounds such as TiS$_2$, V$_2$O$_5$, MgVO$_3$, MoS$_2$, MgV$_2$O$_5$, MoO$_3$, Spinel structured compounds such as CuCr$_2$S$_4$, MgCr$_2$S$_4$, MgMn$_2$O$_4$, Mg$_2$MnO$_4$, NASICON structured compounds such as MgFe$_2$(PO$_4$)$_3$ and MgV$_2$(PO$_4$)$_3$, Olivine structured compounds such as MgMnSiO$_4$ and MgFe$_2$(PO$_4$)$_2$, Tavorite structured compounds such as Mg$_{0.5}$VPO$_4$F, pyrophosphates such as TiP$_2$O$_7$ and VP$_2$O$_7$, and fluorides such as FeF$_3$.

According to conventional practice, the positive electrode may also contain an electronically conductive additive, such as carbon black, Super P, Super C65, Ensaco black, Ketjen black, acetylene black, synthetic graphite such as Timrex SFG-6, Timrex SFG-15, Timrex SFG-44, Timrex KS-6, Timrex KS-15, Timrex KS-44, natural flake graphite, carbon nanotubes, fullerenes, hard carbon, and mesocarbon microbeads.

Additionally, the positive electrode may further comprise a polymer binder. Non-limiting examples of polymer binders include poly-vinylidene fluoride (PVdF), poly(vinylidene fluoride-co-hexafluoropropene) (PVdF-HFP), Polytetrafluoroethylene (PTFE), Kynar Flex 2801, Kynar Powerflex LBG, and Kynar HSV 900, and Teflon. Poly-vinylidene fluoride (PVdF) is a preferred binder.

Solvents suitable in the Mg battery may be any aprotic solvent which is compatible with magnesium and the other components of the battery, including compounds of formula (I). Conventional solvents selected from the group consisting of tetrahydrofuran. 2-methyl tetrahydrofuran, dimethoxyethane, glyme, monoglyme, dimethyl glycol, dimethyl ether, diethyl ether, ethyl glyme, diglyme, proglyme, ethyl diglyme, triglyme, butyl diglyme, tetraglyme, polyglyme, highlyme, and combinations thereof may be included in the claimed Mg battery.

Halide containing solvents and halide salts are preferably not included in the Mg battery as described above.

The Mg battery according to the invention may be constructed by methods which are conventionally known and may be a button or coin cell battery consisting of a stack of negative electrodes, porous polypropylene or glass fiber separators, and positive electrode disks in a can base onto which a can lid is crimped. Alternatively, the Mg battery may be a stacked cell battery. In other embodiments, the Mg battery may be a prismatic, or pouch, cell consisting of one or more stacks of negative electrode, porous polypropylene or glass fiber separator, and positive electrode sandwiched between current collectors, as described above. The stack(s) may be folded within a polymer coated aluminum foil pouch, vacuum and heat dried, filled with electrolyte, and vacuum and heat sealed. In other embodiments, the Mg battery may be a prismatic, or pouch, bi-cell consisting of one or more stacks of a positive electrode which is coated with active material on both sides and wrapped in porous polypropylene or glass fiber separator, and a negative electrode folded around the positive electrode. The stack(s) are folded within a polymer coated aluminum foil pouch, dried under heat and/or vacuum, filled with electrolyte, and vacuum and heat sealed. In some embodiments of the prismatic or pouch cells described herein, an additional tab composed of a metal foil or carbonaceous material may be affixed to the current collector by laser or ultrasonic welding, adhesive, or mechanical contact, in order to connect the electrodes to the device outside the packaging. In other embodiments, the Mg battery disclosed herein is a wound or cylindrical cell consisting of wound layers of one or more stacks of a positive electrode which is coated with active material on one or both sides, sandwiched between layers of porous polypropylene or glass fiber separator, and a negative electrode. The stack(s) are wound into cylindrical roll, inserted into the can, dried under heat and/or vacuum, filled with electrolyte, and vacuum and welded shut. In some embodiments of the cylindrical cells described herein, an additional tab composed of a metal foil or carbonaceous material may be affixed to the current collector by laser or ultrasonic welding, adhesive, or mechanical contact, in order to connect the electrodes to the device outside the packaging.

The stainless steel component, including the current collector may be constructed of any of the conventionally known stainless types, including 302, 304, 305, 316 and 384.

Having generally described this invention, a further understanding can be obtained by reference to certain specific examples which are provided herein for purposes of illustration only and are not intended to be limiting unless otherwise specified. Skilled artisans will recognize the utility of the devices of the present invention as a battery as well as the general utility of the electrolyte system described herein.

EXAMPLES

Synthesis of (Mg$_2$(μ-Cl)$_3$.6THF)(BPh)$_4$ electrolyte

In an argon-filled glovebox, PhMgCl (2 M solution in THF, 3.80 mL,) was mixed with BPh$_3$ (0.5 M solution in THF, 10 mL) in a 20 ml screw capped vial. The vial was immediately capped and vigorously stirred for 24 hours. The crystals were formed by slow diffusion of anhydrous hexane (Sigma-Aldrich, 15 mL) and were washed with hexane and dried under vacuum to furnish off white crystalline product $(Mg_2(\mu\text{-Cl})_3 \cdot 6THF)(BPh)_4$.

Crystal Summary of $(Mg_2(\mu\text{-Cl})_3 \cdot 6THF)(Bph_4)$

Crystal data for $C_{48}H_{68}BCl_3Mg_2O_6$; $M_r=906.80$; Monoclinic; space group $P2_1/c$; $a=16.4151(16)$ Å; $b=16.5787(16)$ Å; $c=18.5617(19)$ Å; $\alpha=90°$; $\beta=109.3640(10)°$; $\gamma=90°$; $V=4765.6(8)$ Å$^3$; $Z=4$; $T=120(2)$ K; $\lambda(Mo\text{-}K\alpha)=0.71073$ Å; $\mu(Mo\text{-}K\alpha)=0.265$ mm$^{-1}$; $d_{calc}=1.264$ g.cm$^{-3}$; 76313 reflections collected; 11872 unique ($R_{int}=0.0351$); giving $R_1=0.0345$, $wR_2=0.0860$ for 9917 data with [I>2σ(I)] and $R_1=0.0443$, $wR_2=0.0925$ for all 11872 data. Residual electron density (e$^-$. Å$^{-3}$) max/min: 1.148/−0.351.

An arbitrary sphere of data were collected on a colorless columnar-like crystal, having approximate dimensions of 0.69×0.22×0.19 mm, on a Bruker APEX-II diffractometer using a combination of ω- and φ-scans of 0.5°. Data were corrected for absorption and polarization effects and analyzed for space group determination. The structure was solved by direct methods and expanded routinely. The model was refined by full-matrix least-squares analysis of F$^2$ against all reflections. All non-hydrogen atoms were refined with anisotropic thermal displacement parameters. Unless otherwise noted, hydrogen atoms were included in calculated positions. Thermal parameters for the hydrogens were tied to the isotropic thermal parameter of the atom to which they are bonded (1.5× for methyl, 1.2× for all others).

Mass Spectroscopy

Electrospray ionization mass spectra were acquired on a Bruker (Billerica, Mass.) MaX is quadrupole-time-of-flight instrument operating in the negative ion mode. Samples dissolved in THF were drawn into a 250 microliter Hamilton (Reno, Nev.) gas tight syringe under a gentle stream of nitrogen gas then directly infused into the ion source via a KD Scientific (Holliston, Mass.) syringe pump operating at a flow rate of 10-20 microliters per minute. Mass spectra were acquired at an acquisition rate of 1 Hz for a total of five minutes over the mass range 50-3000 u, and results were processed using Bruker DataAnalysis software version 4.0.

Electrochemistry

All electrolytes were evaluated at 0.2 M. Cyclic voltammograms were obtained using a BioLogic SAS, model VMP3, Science Instruments potentiostat in a conventional 3-electrode cell at room temperature (21° C.) with a Pt working electrode or stainless stainless working electrode with 0.02 cm$^2$ surface area, a Mg wire reference electrode, and a Mg ribbon counter electrode at a scan rate of 25 mV s$^{-1}$. Data was processed with EC-Lab Software V10.02 with the corresponding VMP3 firmware, provided by Science Instruments.

TABLE 1

Crystal data and structure refinement for $(Mg_2(\mu\text{-Cl})_3 \cdot 6THF)(BPh_4)$.

| | |
|---|---|
| Identification code | $(Mg_2(\mu\text{-Cl})_3 \cdot 6THF)(BPh_4)$ |
| Empirical formula | $C_{48}H_{68}BCl_3Mg_2O_6$ |
| Formula weight | 906.80 |
| Temperature | 120(2) K |
| Wavelength | 0.71073 Å |
| Crystal system | Monoclinic |
| Space group | $P2_1/c$ |

TABLE 1-continued

Crystal data and structure refinement for $(Mg_2(\mu\text{-Cl})_3 \cdot 6THF)(BPh_4)$.

| | |
|---|---|
| Unit cell dimensions | $a = 16.4151(16)$ Å $\alpha = 90°$ |
| | $b = 16.5787(16)$ Å $\beta = 109.3640(10)°$ |
| | $c = 18.5617(19)$ Å $\gamma = 90°$ |
| Volume | 4765.6(8) Å$^3$ |
| Z | 4 |
| Density (calculated) | 1.264 g·cm$^{-3}$ |
| Absorption coefficient (μ) | 0.265 mm$^{-1}$ |
| F(000) | 1936 |
| Crystal size | 0.69 × 0.22 × 0.19 mm$^3$ |
| θ range for data collection | 1.69 to 28.35° |
| Index ranges | $-21 \leq h \leq 21, -22 \leq k \leq 22, -24 \leq l \leq 24$ |
| Reflections collected | 76313 |
| Independent reflections | 11872 [$R_{int} = 0.0351$] |
| Completeness to θ = 28.36° | 99.7% |
| Absorption correction | Numerical |
| Max. and min. transmission | 1.0000 and 0.9396 |
| Refinement method | Full-matrix least-squares on F$^2$ |
| Data/restraints/parameters | 11872/0/541 |
| Goodness-of-fit on F$^2$ | 1.030 |
| Final R indices [I > 2σ(I)] | $R_1 = 0.0345$, $wR_2 = 0.0860$ |
| R indices (all data) | $R_1 = 0.0443$, $wR_2 = 0.0925$ |
| Largest diff. peak and hole | 1.148 and −0.351 e$^-$.A$^{-3}$ |

The invention claimed is:

1. A magnesium battery, comprising:
   a negative electrode comprising magnesium;
   a positive electrode which is stable to 2.6 E.V. vs. Mg;
   a solvent; and
   an electrolyte of formula (I) which is soluble in the solvent:

$$[Mg_2(\mu\text{-Cl})_3 \cdot 6THF][BR_4] \quad (I)$$

wherein
   R is each independently a C(1-12) alkyl or C(6-10) aryl group, optionally substituted with alkoxy, cyano, nitro or C(1-6) alkyl groups, and
   wherein
   the electrolyte of formula (I) is a crystallized salt isolated from a solution comprising tetrahydrofuran.

2. The magnesium battery, according to claim 1, wherein the negative electrode is magnesium.

3. The magnesium battery, according to claim 1, wherein the positive electrode active material comprises at least one component selected from the group consisting of Sulfur, graphitic carbon, carbon fiber, glassy carbon, pyrolitic carbon, amorphous carbon, $Mo_6S_8$, $MnO_2$, CuS, $Cu_2S$, $Ag_2S$, $CrS_2$, $VOPO_4$, $TiS_2$, $V_2O_5$, $MgVO_3$, $MoS_2$, $MgV_2O_5$, $MoO_3$, $CuCr_2S_4$, $MgCr_2S_4$, $MgMn_2O_4$, $Mg_2MnO_4$, $MgFe_2(PO4)_3$, $MgV_2(PO_4)_3$, $MgMnSiO_4$, $MgFe_2(PO_4)_2$, $Mg_{0.5}VPO_4F$, $TiP_2O_7$, $VP_2O_7$ and $FeF_3$.

4. The magnesium battery, according to claim 3, wherein the positive electrode further comprises a polymeric binder selected from the group consisting of poly-vinylidene fluoride (PVdF), poly(vinylidene fluoride-co-hexafluoropropene) (PVdF-HFP) and Polytetrafluoroethylene (PTFE).

5. The magnesium battery, according to claim 1, wherein the solvent is selected from the group consisting of tetrahydrofuran, 2-methyl tetrahydrofuran, dimethoxyethane, glyme, monoglyme, dimethyl glycol, ethylene glycol dimethyl ether, diethyl ether, ethyl glyme, diglyme, proglyme, ethyl diglyme, triglyme, butyl diglyme, tetraglyme, polyglyme, higlyme, and a mixture thereof.

6. The magnesium battery, according to claim 1, wherein R of formula (I) is methyl, ethyl or propyl.

7. The magnesium battery, according to claim 1, wherein R of formula (I) is phenyl, tolyl or xylyl.

8. The magnesium battery, according to claim 1, wherein the battery comprises at least one stainless steel component.

9. The magnesium battery, according to claim 8, wherein the at least one stainless steel component is a current collector for the positive electrode.

10. The magnesium battery, according to claim 1, wherein the negative electrode is magnesium,
the positive electrode comprises a stainless steel current collector coated with a composition comprising sulfur, and
the electrolyte of formula (I) is $$[Mg_2(\mu\text{-Cl})_3 \cdot 6THF][B(C_6H_5)_4] \quad (I).$$

11. The magnesium battery, according to claim 10, wherein the solvent is tetrahydrofuran.

12. The magnesium battery, according to claim 10, wherein the composition comprising sulfur, further comprises a carbon fiber and a binder.

13. The magnesium battery, according to claim 12, wherein the binder is poly-vinylidene fluoride (PVdF).

14. An electrolyte of formula (I):

$$[Mg_2(\mu\text{-Cl})_3 \cdot 6THF][BR_4] \quad (I)$$

obtained by reaction of a Grignard reagent or a Hauser base with a boron compound of formula (II), and $$BR_3 \quad (II)$$

isolating a crystallized solid of formula (I),
wherein
R is each independently a C(1-12) alkyl or C(6-10) aryl group, optionally substituted with alkoxy, cyano, nitro or C(1-6) alkyl groups.

15. The electrolyte of claim 14, wherein R is phenyl, tolyl or xylyl.

16. The electrolyte of claim 14, wherein R is phenyl.

17. A magnesium battery, comprising:
a magnesium negative electrode;
a positive electrode having a stainless steel current collector; and
the electrolyte of claim 14.

18. A magnesium battery, comprising:
a magnesium negative electrode;
a positive electrode having a stainless steel current collector; and
the electrolyte of claim 16.

* * * * *